United States Patent
Henniges et al.

(10) Patent No.: US 7,179,914 B2
(45) Date of Patent: Feb. 20, 2007

(54) PROCESS FOR THE PRODUCTION OF 4-ALKYLPYRIMIDINE

(75) Inventors: Hans Henniges, Frankfurt (DE); Hans-Juergen Pitz, Roesrath (DE); Christoph Theis, Niederkassel (DE); Manfred Neumann, Marl (DE)

(73) Assignee: Degussa AG, Duesseldorf (DE)

( * ) Notice: Subject to any disclaimer, the term of this patent is extended or adjusted under 35 U.S.C. 154(b) by 388 days.

(21) Appl. No.: 10/778,254

(22) Filed: Feb. 17, 2004

(65) Prior Publication Data
US 2004/0225126 A1 Nov. 11, 2004

(30) Foreign Application Priority Data
Feb. 17, 2003 (DE) .................. 103 06 445

(51) Int. Cl.
*C07D 239/26* (2006.01)
(52) U.S. Cl. ..................................... 544/242
(58) Field of Classification Search ................ 544/242
See application file for complete search history.

(56) References Cited

U.S. PATENT DOCUMENTS

2004/0044209 A1   3/2004   Guthner et al.

FOREIGN PATENT DOCUMENTS

| DE | 100 02 835 | 12/2001 |
|---|---|---|
| JP | 49-124081 | 11/1974 |
| JP | 8-198858 | 8/1996 |

OTHER PUBLICATIONS

H. Bredereck, et al., Angew. Chem., vol. 68, No. 4, pp. 151-152, "Neue Pyrimidin-Synthese Aus β-Dicarbonyl-Verbindungen Und Formamid", 1956.
H. Bredereck, et al., Chemische Berichte, 90, pp. XXXIX-XIII and 942-952, "Eine Neue Pyrimidin-Synthese$^2$", 1957.
H. Bredereck, J. Wiley and Sons, Organic Syntheses, Collective vol. 5, pp. xi-xiv, 794-796, "4-Methylpyrimidine", 1973.

*Primary Examiner*—Deepak Rao
(74) *Attorney, Agent, or Firm*—Oblon, Spivak, McClelland, Maier & Neustadt, P.C.

(57) ABSTRACT

4-alkylpyrimidine is produced by reacting formamide with a formyl methyl alkyl ketone diacetal without the addition of water at a temperature that allows removal of the 4-alkylpyrimidine from the reaction mixture by distillation. The process is readily applicable on an industrial scale and succeeds without the addition of water or ammonium chloride as a catalyst and permits the production of 4-alkylpyrimidine in good yields and excellent purities without time-consuming extraction steps.

16 Claims, No Drawings

PROCESS FOR THE PRODUCTION OF 4-ALKYLPYRIMIDINE

BACKGROUND OF THE INVENTION

1. Field of the Invention

The present invention relates to a process for the production of 4-alkylpyrimidines, particularly 4-methylpyrimidine.

2. Discussion of the Background

4-Methylpyrimidine is an intermediate for the synthesis of biologically active substances, such as e.g. plant protection agents or pharmaceuticals. Bredereck et al. developed syntheses for producing 1,3-diazoles starting from 1,3-dicarbonyl compounds and formamidine (Angew. Chem. 1956, 68, 151; Chem. Ber. 1957, 90, 942). According to a synthesis by Bredereck et al. (Org. Synth. Coll. Vol. V, 794, Wiley 1973), formamide can be reacted with 4,4-dimethoxy-2-butanone (formyl acetone dimethylacetal) in the presence of ammonium chloride and water at 180–190° C. to form 4-methylpyrimidine as follows:

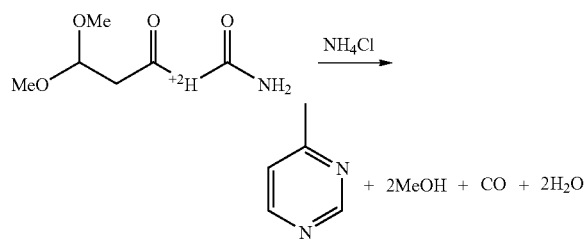

The above method has a number of disadvantages. On hand, the yield is modest by industrial standards, at 54–63%. On the other hand, to achieve the yield at all, an excess of formamide of 6:1 has to be used, based on 4,4-dimethoxy-2-butanone, although only 2 moles are needed. In addition, it is necessary to add a slightly acidic catalyst at 30 mole %, based on 4,4-dimethoxy-2-butanone. During the subsequent distillation, ammonium salts sublime into the gas space and precipitate at a cooler point in the reaction apparatus, which is a great problem on an industrial scale as these salts can, for example, clog up reactor condensers and lead to production failures. The workup of the distillate, which is conventional in the Bredereck method, utilizes a lengthy extraction with chloroform to separate the 4-methylpyrimidine from the water of reaction and methanol. This inefficient operation is necessary because of the very good water solubility of 4-methylpyrimidine.

Other production methods for pyrimidines start from formamidinium salts, which has the disadvantage in principle that formamide generally has to be released by adding a base, conventionally an alkali alcoholate (e.g. sodium methylate) (e.g. JP 08198858, JP 49124081). In these process variants too, the yields that can be achieved are generally unsatisfactory. Thus, in a patent published only recently, a method is employed in which formamidinium acetate is used and then extraction is performed with tert-butyl methyl ether for a total of 20–26 h. The raw material obtainable in this way could be purified by distillation only with difficulty. Yields of 34 to 50% with contents of 95–98% were typical. In addition, mixed fractions were obtained with contents of 88 to 94%, which in turn contributed a further approx. 10% to the total yield (DE 10002835).

SUMMARY OF THE INVENTION

It is therefore an object of the present invention to provide a process for the production of 4-alkylpyrimidines, which in particular allows a higher yield of product compared to known processes and helps to avoid the apparatus-related disadvantages of the Bredereck process. On an industrial scale in particular, this process should allow 4-alkylpyrimidines to be produced in an economically and ecologically advantageous manner.

This and other objects have been achieved by the present invention the first embodiment of which includes a process for the production of a 4-alkylpyrimidine, comprising:

reacting formamide with a formyl methyl alkyl ketone diacetal without the addition of water at a temperature that allows removal of said 4-alkylpyrimidine from the reaction mixture by distillation.

DETAILED DESCRIPTION OF THE INVENTION

In a process for the production of 4-alkylpyrimidines starting from formyl methyl alkyl ketone diacetals with formamide, by taking an initial charge of formamide and reacting this with formyl methyl alkyl ketone diacetals without adding water, at temperatures at which the 4-alkylpyrimidine can be removed from the reaction mixture by distillation, the desired products are obtained in surprisingly high yields. The formyl methyl alkyl ketone diacetal can be metered into the reaction mixture by any method. It can be added to the reaction mixture all at once, right at the beginning, or, advantageously, continuously at the rate at which it is consumed by the reaction.

The reaction forming the subject-matter of the present invention is applicable to all 4-alkylpyrimidines with small, obvious variations. Advantageously, alkyl refers to a $(C_1-C_{15})$ alkyl radical, particularly advantageously a methyl radical. In this case, 4,4-dimethoxy-2-butanone (formyl acetone dimethylacetal) is used as the formyl methyl alkyl ketone diacetal.

The temperature of the reaction depends in principle on the product formation and isolation. The reaction is advantageously performed at temperatures of >150° C., preferably >170° C. and particularly preferably at approx. 190° C. The reaction temperature includes all values and subvalues therebetween, especially including 155, 160, 165, 170, 175, 180 and 185° C.

The product mixture generated can be worked up by any method. Preferred are for example, extraction, chromatography, crystallization, etc. Particularly preferably, the product can be purified by fractional distillation.

The water of reaction that forms impedes effective product formation in that the water and the product form an azeotropic mixture. To obtain an anhydrous product, the water of reaction therefore has to be removed from the reaction mixture. This can take place by any means available for this purpose to the person skilled in the art, such as e.g. pervaporation through a semi-permeable membrane, by binding the water with a molecular sieve, or advantageously in that, before purification, a water-binding agent is added to the product mixture. Any water-binding agent may be used. Preferred water-binding agents are KOH, $P_2O_5$, $PCl_3$ or ortho esters, etc. The addition of trimethyl orthoformate is especially preferred.

In the process according to the present invention for the production of 4-methylpyrimidin, the preferred method is as follows. Formamide is initially charged into a reaction vessel in 4 equivalents and heated to about 190° C. with ammonium chloride without the addition of water. Formyl methyl alkyl ketone diacetal is then metered in. At the high temperature, controlled by the addition of formyl methyl alkyl, ketone diacetal, a methanol/water/4-alkylpyrimidine/ formamide mixture is distilled off continuously. As a result, the product is immediately removed from the high reaction temperatures and thus from possible secondary reactions. The conversion is practically complete. The selectivity of the pyrimidine formation in the reaction is often more than 80% (according to GC in the distillate). The selectivity includes all values and subvalues therebetween, especially including 80, 82, 84, 86, 88, 90, 92, 94, 96, 98 and 99%. Ammonium salts are formed to a much lesser extent. Nevertheless, the whole of the reaction apparatus should be operated at >50° C. to prevent condensation of ammonium salts. The distillate obtained consists substantially of ammonium formate/methanol/water/4-methylpyrimidine/formamide. By simply heating the distillate to about 60° C., the ammonium formate can be driven off.

Trimethyl orthoformate is added to the residue, in a sufficient quantity for all the water of reaction to be bound. Methyl formate and methanol are then distilled off before the 4-alkylpyrimidine distils over.

The present invention allows the valuable intermediates to be synthesized without any great apparatus-related difficulties by a method that is substantially simplified, and therefore more advantageous, compared with the prior art. Product yields can be approx. 80% pure substance and more, calculated overall. The overall yield includes all values and subvalues, especially 70, 75, 80, 85, 90, 95 and 99%. The purity includes all values and subvalues, especially including 90, 92, 94, 96, 98, 99 and 99.5%.

Alkyl radical preferably means a linear or branched, optionally mono- or polyunsaturated, $(C_1-C_{15})$ alkyl radical, such as e.g. methyl, ethyl, propyl, isopropyl, butyl, tert.-butyl, sec-butyl, isobutyl, pentyl, hexyl, dodecyl, etc.

Having generally described this present invention, a further understanding can be obtained by reference to certain specific examples which are provided herein for purposes of illustration only, and are not intended to be limiting unless otherwise specified.

EXAMPLE

Reaction of Formamide and 4,4-dimethoxy-2-butanone:

272 g (6.0 mol) of formamide were initially charged into a dry glass reactor with a double-wall jacket and heated to 190° C. (bottom temperature), stirring well. 209 g (1.5 mol) of 95% 4,4-dimethoxy-2-butanone were then metered-in continuously within 3 h using a hose pump. At the same time, through a simple, jacketed riser tube and a descending condenser thermostatically controlled at 50° C., 342 g of a yellow reaction distillate, consisting of methanol, water, 4-methylpyrimidine and ammonium formate, were removed overhead. The overhead temperature fell significantly from approx. 158° C. almost immediately after the end of the addition. The mixture was then left for a further 30 min for after-reaction.

The ammonium formate (approx. 15 g) formed as a by-product during the reaction tends to precipitate in the gas space or, if the cooling is too strong, to sediment on the cooling side. At the rate of addition of 4,4-dimethoxy-2-butanone mentioned, the distillate stream flushed the salt into the receiver.

The oil bath temperatures during the reaction were 215–220° C., bottom temperatures 188–196° C., and the overhead temperatures rose up to approx. 158° C.

Salt Separation:

Before the water of reaction is removed, it is essential to remove the (partially precipitated) ammonium salt, as otherwise, this sublimes into the gas space during the distillation of the target product and is found in the product distillate again at the end, with contents of 2–3%.

The flask with the reaction distillate (342 g) was provided in the laboratory with a condenser heated to 125° C. and freed from approx. 15 g of ammonium salt at bottom temperatures of up to 60° C. (oil bath up to 68° C.) and overhead temperatures up to 39° C. Duration 1.5 h. The residue consisting of 4-methylpyrimidine, water and methanol was 327 g after the salt separation. The 4-methylpyrimidine contents were typically 34–36 wt. %. The proportion of water was approx. 12%.

Separation of Water and Distillation:

To remove the water from the mixture of 4-methylpyrimidine (approx. 34%), water (approx. 12%) and methanol, a quantity of 250 g trimethyl orthoformate (TMOF) (2.35 mol) was added to the residue from the salt separation (327 g) and the mixture was stirred for 30 min at RT.

The subsequent distillation of low-boilers took place under standard pressure (reduction 5:1) in a 60 cm packed column (with Moltifill packings, 10 theor. plates). The oil bath temperature was increased during this operation from 89 to 160° C. At the same time, the bottom temperature rose from 69 to 126° C. and the overhead temperature from 34 to 65° C., and then fell again (fraction 1, approx. 340 g). The distillation of the target product was performed in the same column at 80 mbar. In the first runnings, the oil bath temperature was raised from 96 to approx. 120° C., the bottom temperature rising from 66 to 81° C. The overhead temperature rose from 31 to 69° C. at the same time (fraction 2, target product first runnings, approx. –16 g). In the main fraction (oil bath temp. 122–162° C., bottom temp. 80–128° C., overhead temp. 69–72° C.) when using first runnings and tails (approx. 35 g) from another batch, processed in the same way, approx. 111 g of target product were obtained with a purity according to GC of >99%. This corresponds to a yield of 79% 4-methylpyrimidine (fraction 3, target product main fraction).

German patent application 103 06 445.1 filed Feb. 17, 2003, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for the production of a 4-alkylpyrimidine, comprising:
   reacting formamide with a formyl methyl alkyl ketone diacetal without the addition of water at a temperature that allows removal of said 4-alkylpyrimidine from the reaction mixture by distillation.

2. The process according to claim 1, wherein said formyl methyl alkyl ketone diacetal is added to the reaction mixture continuously at the rate at which it is consumed by the reaction between formamide and formyl methyl alkyl ketone diacetal.

3. The process according to claim 1, wherein said formyl methyl alkyl ketone diacetal is formyl acetone dimethylacetal.

4. The process according to claim 1, wherein said reaction is performed at a temperature of >150° C.

5. The process according to claim 1, wherein said reaction is performed at a temperature of >170° C.

6. The process according to claim 1, wherein said reaction is performed at about 190° C.

7. The process according to claim 1, wherein said 4-alkylpyrimidine is purified by fractional distillation.

8. The process according to claim 1, wherein said 4-alkylpyrimidine is purified and wherein, before purification, a water-binding agent is added to said 4-alkylpyrimidine in its unpurified form.

9. The process according to claim 1, wherein the alkyl group in said 4-alkylpyrimidine is a ($C_1$–$C_{15}$) alkyl radical.

10. The process according to claim 1, wherein the alkyl group in said 4-alkylpyrimidine is a methyl radical.

11. The process according to claim 8, wherein said water-binding agent is selected from the group consisting of KOH, $P_2O_5$, $PCl_3$ and ortho esters.

12. The process according to claim 8, wherein said water-binding agent is trimethyl orthoformate.

13. The process according to claim 1, wherein four equivalents of formamide react with formyl methyl alkyl ketone diacetal.

14. The process according to claim 1, wherein said 4-alkylpyrimidine is distilled of in form of a methanol/water/4-alkylpyrimidine/formamide mixture.

15. The process according to claim 1, wherein a selectivity of the pyrimidine formation in the reaction is more than 80%.

16. The process according to claim 1, having an overall yield of 4-alkylpyrimidine of 80%.

* * * * *